US007696372B2

United States Patent
Guo et al.

(10) Patent No.: US 7,696,372 B2
(45) Date of Patent: Apr. 13, 2010

(54) PROCESS FOR PREPARING R-GOSSYPOL L-PHENYLALANINOL DIENAMINE

(75) Inventors: Ming Guo, San Diego, CA (US); Shuguang Zhu, San Diego, CA (US); Laure Navarre, Lyons (FR); Régis Périon, Le Mans (FR)

(73) Assignee: Ascenta Therapeutics, Inc., Malvern, PA (US)

( * ) Notice: Subject to any disclaimer, the term of this patent is extended or adjusted under 35 U.S.C. 154(b) by 0 days.

(21) Appl. No.: 12/285,291

(22) Filed: Oct. 1, 2008

(65) Prior Publication Data

US 2009/0088590 A1    Apr. 2, 2009

Related U.S. Application Data

(60) Provisional application No. 60/976,637, filed on Oct. 1, 2007, provisional application No. 61/129,082, filed on Jun. 4, 2008.

(51) Int. Cl.
*C07C 227/38* (2006.01)
*C07C 227/40* (2006.01)
*C07C 227/42* (2006.01)
*C07C 45/78* (2006.01)
*C07C 45/81* (2006.01)

(52) U.S. Cl. .................................. 560/35; 568/438
(58) Field of Classification Search ................. None
See application file for complete search history.

(56) References Cited

U.S. PATENT DOCUMENTS

| 5,059,717 A * | 10/1991 | Ibragimov et al. | 568/438 |
| 2005/0027000 A1 | 2/2005 | Reed et al. | |
| 2005/0234135 A1 * | 10/2005 | Wang et al. | 514/700 |

FOREIGN PATENT DOCUMENTS

| CN | 1033795 A | 7/1989 |
| JP | 01132542 A | 5/1989 |

OTHER PUBLICATIONS

Dowd, M.K., "Preparation of Enantiomeric Gossypol by Crystallization," *Chirality 15*:486-493, Wiley, Hoboken, NJ USA (2003).
Fish, R.G., et al., "The Photo-epimerisation of Gossypol Schiff's Bases," *Tetrahedron: Asymmetry 6*:873-876, Elsevier Science Ltd., Great Britain (1995).
Huang, L., et al., "Resolution of Racemic Gossypol," *Journal of Ethnopharmacology 20*:13-20, Elsevier Science Publishers Ireland Ltd., Ireland (1987).
Kai, Z.D., et al., "Resolution of Racemic Gossypol," *J. Chem Soc., Chem. Commun. 1985*:168-169, RSC Publishing, London (1985).

Kim, I.C., et al., "Comparative in Vitro Spermicidal Effects of (±)-Gossypol, (+)-Gossypol, (-)-Gossypol and Gossypolone," *Contraception 30*:253-259, Elsevier, Inc., Amsterdam, The Netherlands (1984).
Matlin, S.A., et al., "Resolution of Gossypol: Analytical and Large-Scale Preparative HPLC on Non-Chiral Phases," *Journal of High Resolution Chromatography & Chromatography Communications 10*:86-91, Dr. Alfred Huethig Publishers, Germany (1987).
Matlin, S.A., et al., "Large-Scale Resolution of Gossypol Enantiomers for Biological Evaluation," *Contraception 37*:229-237, Elsevier, Inc., Amsterdam, The Netherlands (1988).
Matlin, S.A. and Zhou, R., "Resolution of Gossypol: Analytical and Preparative HPLC," *Journal of High Resolution Chromatography & Chromatography Communications 7*:629-630, Dr. Alfred Huethig Publishers, Germany (1984).
Sampath, D.S. And Balaram, P., "Resolution of racemic gossypol and interaction of individual enantiomers with serum albumins and model peptides," *Biochimica et Biophysica Acta 882*:183-186, Elsevier, Inc., Amsterdam, the Netherlands (1986).
Sampath, D.S. and Balaram, P., "A Rapid Procedure for the Resolution of Racemic Gossypol," *J. Chem. Soc., Chem. Commun. 1986*:649-650, RSC Publishing, London (1986).
Shelley, M.D., et al., "Stereo-specific cytotoxic effects of gossypol enantiomers and gossypolone in tumour cell lines," *Cancer Letters 135*:171180, Elsevier Science Publishers Ireland Ltd., Ireland (1999).
Yikang, S., et al., "Studies on Resolution of Racemic Gossypol," *Scientia Sinica XXX*:297-303, Science Press, Beijing, China (1987).
Zhou, R.H. And Lin, X.D., "Isolation of (-)-Gossypol from Natural Plant," *Contraception 37*:239-245, Elsevier, Inc., Amsterdam, The Netherlands (1988).
International Search Report for International Application No. PCT/US08/11327, Dec. 11, 2008, ISA/US, Alexandria, VA USA.
English translation of Japanese Unexamined Patent Application Publication No. H1-132542 (cited as Document FP1).
English translation of Chinese Patent Application No. 87105990 (cited as Document FP2).

\* cited by examiner

*Primary Examiner*—Brian J Davis
(74) *Attorney, Agent, or Firm*—Sterne, Kessler, Goldstein & Fox P.L.L.C.

(57) ABSTRACT

This invention relates to a process for preparing R-gossypol L-phenylalaninol dienamine using non-chromatographic purification methods. In particular, the invention is directed to resolution of R- and S-gossypol L-phenylalaninol dienamine by crystallization. R-gossypol L-phenylalaninol dienamine is a useful intermediate for the preparation of R-(−)-gossypol and R-(−)-gossypol acetic acid co-crystal. R-(−)-Gossypol acetic acid and its co-crystal is useful for inducing apoptosis in cells and for sensitizing cells to the induction of apoptotic cell death.

25 Claims, No Drawings

PROCESS FOR PREPARING R-GOSSYPOL L-PHENYLALANINOL DIENAMINE

BACKGROUND OF THE INVENTION

1. Field of the Invention

This invention relates to a process for preparing R-gossypol L-phenylalaninol dienamine using non-chromatographic purification methods. In particular, the invention is directed to resolution of R- and S-gossypol L-phenylalaninol dienamine by crystallization. R-gossypol L-phenylalaninol dienamine is a useful intermediate for the preparation of R-(−)-gossypol and R-(−)-gossypol acetic acid co-crystals. R-(−)-Gossypol acetic acid and its co-crystals are useful for inducing apoptosis in cells and for sensitizing cells to the induction of apoptotic cell death.

2. Background of the Invention

US 2005/0234135 A1 discloses R-(−)-gossypol in the form of acetic acid co-crystals and its use as an inhibitor anti-apoptotic Bcl-2 family proteins. By inhibiting anti-apoptotic Bcl-2 family proteins, R-(−)-gossypol sensitizes cells to inducers of apoptosis and, in some instances, itself induces apoptosis. Because of the potential utility of R-(−)-gossypol and its acetic acid co-crystal in the treatment of cancer and other diseases, there exists a need to develop a practical synthetic route to produce substantial quantities of this drug substance.

SUMMARY OF THE INVENTION

The invention confronts the problem of providing a process for obtaining R-(−)-gossypol and its acetic acid co-crystal with high purity. The invention is based on the unexpected discovery that R-gossypol L-phenylalaninol dienamine can be isolated in high diastereomeric purity from a mixture of R- and S-gossypol L-phenylalaninol dienamine by crystallization in a solvent system comprising acetonitrile and water. This obviates the need for chromatographic resolution and is more amenable to large-scale production of R-gossypol L-phenylalaninol diimine and, ultimately, R-(−)-gossypol and its acetic acid co-crystal.

DETAILED DESCRIPTION OF THE INVENTION

The present invention relates to a process for preparing R-gossypol L-phenylalaninol dienamine using non-chromatographic purification methods. In particular, the invention is directed to resolution of R- and S-gossypol L-phenylalaninol dienamine by crystallization in a solvent system comprising acetonitrile and water.

Applicants have found that crystallization of a mixture of R- and S-gossypol Schiff bases, and tautomers thereof, to provide the R-isomer substantially free from the S-isomer was challenging and unpredictable. To this end, an assortment of solvent systems were surveyed in an effort to identify one useful for resolving R- and S-gossypol L-phenylalanine diimine. These studies did not succeed in identifying conditions suitable to produce R-gossypol L-phenylalanine diimine substantially free from S-gossypol L-phenylalanine diimine. Solvent systems such as 1:2 dichloromethane:isopropyl alcohol, 1:1 dichloromethane:isopropyl alcohol, 1:2 dichloromethane:methanol, 1:5:1.5 dichloromethane:hexane:heptane, 2:1 methanol:hexane, 2:1 ethanol:hexane, toluene, 1:1 toluene:heptane, acetonitrile, 10:1 acetonitrile:water, tert-butyl methyl ether and tert-butyl methyl ether:heptane led to modest diastereomeric enrichment in favor of R-gossypol L-phenylalanine diimine. Solvent systems such as 1:2 dichloromethane:ethanol and 2:1 methanol:water led to no diastereomeric enrichment. Crystal formation was not observed in 2:1 dichloromethane:isopropyl alcohol and 2:1 water:tetrahydrofuran. Three successive crystallizations in 1:2 dichloromethane:isopropanol did not significantly improve the diastereomeric ratio. These data are presented in Example 2.

Experiments aimed at resolving R- and S-gossypol L-phenylalaninol dienamine were also investigated. Crystallization attempts in solvent systems such as methyl alcohol, isopropyl alcohol, acetone, toluene, acetonitrile, 1:1 toluene:heptane, 2:1 tert-butyl methyl ether:heptane, 2:1 methanol:hexane, 1:1 dichloromethane:hexane, 5:1 tetrahydrofuran:water and 1:1 methanol:water resulted in either no enrichment in diastereomeric purity or no crystal formation. In contrast, crystallization in 5:1 acetonitrile:water resulted in a striking improvement in diastereomeric purity favoring R-gossypol L-phenylalaninol dienamine. This unexpected finding was refined to produce a novel, reproducible process for the preparation R-gossypol L-phenylalaninol dienamine. These data are presented in Examples 4 to 8.

In one embodiment, R-gossypol L-phenylalaninol dienamine is prepared from a mixture of R- and S-gossypol L-phenylalaninol dienamine via a process comprising crystallizing said mixture from a solvent system comprising acetonitrile and water and isolating crystalline R-gossypol L-phenylalaninol dienamine substantially free from said S-gossypol L-phenylalaninol dienamine. In one embodiment, crystalline R-gossypol L-phenylalaninol dienamine is isolated by filtration. In another embodiment, crystalline R-gossypol L-phenylalaninol dienamine is isolated by centrifugation.

In one embodiment, the solvent system used to crystallize R-gossypol L-phenylalaninol dienamine substantially free from S-gossypol L-phenylalaninol dienamine, comprises acetonitrile and water in a ratio of about 10:1 to about 5:2. In another embodiment, the solvent system used to crystallize R-gossypol L-phenylalaninol dienamine substantially free from S-gossypol L-phenylalaninol dienamine, comprises acetonitrile and water in a ratio of about 5:1. In another embodiment, the solvent system used to crystallize R-gossypol L-phenylalaninol dienamine substantially free from S-gossypol L-phenylalaninol dienamine, comprises acetonitrile and water in a ratio of about 5:1.5. In another embodiment, the solvent system used to crystallize R-gossypol L-phenylalaninol dienamine substantially free from S-gossypol L-phenylalaninol dienamine, comprises acetonitrile and water in a ratio of about 5:2. In a further embodiment, the solvent system used to crystallize R-gossypol L-phenylalaninol dienamine substantially free from S-gossypol L-phenylalaninol dienamine comprises acetonitrile and water in a ratio of 5:1.

In one embodiment, crystalline R-gossypol L-phenylalaninol dienamine is recrystallized one or more times until the desired level of purity is achieved. In a further embodiment, crystalline R-gossypol L-phenylalaninol dienamine is recrystallized in a solvent system comprising acetonitrile and water.

In one embodiment, isolated crystalline R-gossypol L-phenylalaninol dienamine is washed one or more times with a solvent system comprising acetonitrile and water. In one embodiment, isolated crystalline R-gossypol L-phenylalaninol dienamine is washed with a solvent system comprising acetonitrile and water in a ratio of about 10:1 to about 5:2. In a further embodiment, isolated crystalline R-gossypol L-phenylalaninol dienamine is washed with a solvent system comprising acetonitrile and water in a ratio of about 5:1. In a further embodiment, isolated crystalline R-gossypol L-phenylalaninol dienamine is washed with a solvent system comprising acetonitrile and water in a ratio of 5:1. In a further embodiment, the crystalline R-gossypol L-phenylalaninol dienamine is dried in vacuo.

In one embodiment, the crystalline R-gossypol L-phenylalaninol dienamine has a purity of about 89%, 90%, 91%, 92%, 93%, 94%, 95%, 96%, 97% 98%, 99% or 99.5%.

In one embodiment, crystalline R-gossypol L-phenylalaninol dienamine comprises about 11%, 10%, 9%, 8%, 7%, 6%, 5%, 4%, 3%, 2%, 1% or 0.5% S-gossypol L-phenylalaninol dienamine or less.

In one embodiment R-gossypol L-phenylalaninol dienamine is prepared by a) condensing gossypol with L-phenylalaninol in acetonitrile to provide a mixture of R- and S-gossypol L-phenylalaninol dienamine; b) adding water the reaction mixture at the completion of the reaction between gossypol and L-phenylalaninol to obtain crystalline R-gossypol L-phenylalaninol dienamine; and c) isolating the crystalline R-gossypol L-phenylalaninol dienamine substantially free from the S-gossypol L-phenylalaninol dienamine. In a further embodiment, the reaction mixture is heated to about 50° C. prior to the addition of water. In a further embodiment, the reaction mixture is cooled to about 5° C. after the addition of water. In a further embodiment, crystalline R-gossypol L-phenylalaninol dienamine is isolated by filtration or centrifugation The term "gossypol," as used herein, refers to a composition comprising the compound of the structure:

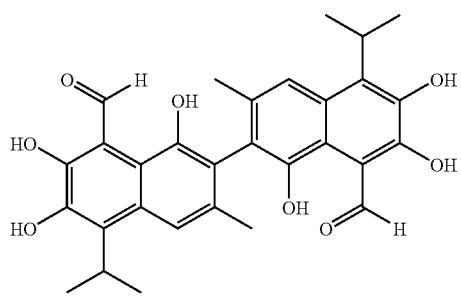

or a tautomer thereof.

Gossypol may be obtained from any one of a number of sources such as the cotton plant, e.g., from cottonseeds or other plant parts. Species of cotton vary widely both in the total content of gossypol and the optical activity of the gossypol. While many species of cotton contain gossypol that is about 50% R-gossypol and 50% S-gossypol, several species have been identified that contain either high levels of (S)-gossypol (e.g., *Gossypium hirsutum, G. arboreum, G. mustelinum, G. anomalum, G. gossypioides, G. capatis-viridis*, (up to about 97% (S)-gossypol)) or high levels of (R)-gossypol (e.g., *G. barbadense, G. darwinii, G. sturtianjm, G. areysianum, G. longicalyx, G. harknessii, G. costulatum* (up to about 65% (R)-gossypol)). See, e.g., Hua et al., *Contraception* 37:239 (1988); Cass et al., *J. Agric. Food Chem.* 52:5822 (2004); Stipanovic et al., *J. Agric. Food Chem.* 53:6266 (2005); Stipanovic et al., 2005 *Beltwide Cotton Conferences*, New Orleans, La., Jan. 4-7, 2005, p. 900. The enantiomeric ratio of gossypol also varies in different parts of the cotton plant. For example, in *G. barbadense* the seeds typically have an excess of (R)-gossypol, but the roots and flowers may contain an excess of (S)-gossypol (Cass et al., *J. Agric. Food Chem.* 52:5822 (2004)). Thus, a strain of cotton or a part thereof that is high in (R)-gossypol may be advantageously used as the source of the gossypol for the present invention.

In one embodiment, gossypol is approximately racemic, i.e., it contains about 50% R-gossypol and about 50% S-gossypol. In another embodiment, gossypol is enriched in R-gossypol. In another embodiment, gossypol is enriched in S-gossypol.

The term "R-gossypol" or "R-(−)-gossypol," as used herein, refers to a composition comprising the compound of structure:

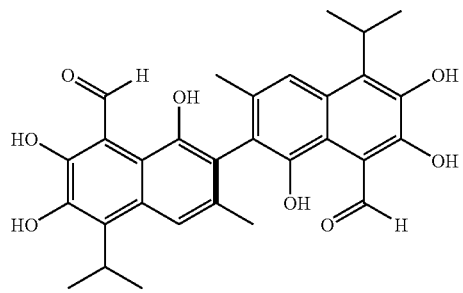

or a tautomer thereof.

The term "S-gossypol" or "S-(+)-gossypol," as used herein, refers to a composition comprising the compound of structure:

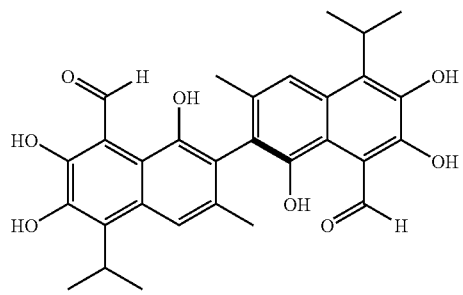

or a tautomer thereof.

The term "gossypol acetic acid," as used herein, refers to a composition comprising gossypol and acetic acid in the form of co-crystals.

In one embodiment, crystallization of R-gossypol L-phenylalaninol dienamine from a mixture of R- and S-gossypol L-phenylalaninol dienamine is induced by seeding with crystalline R-gossypol L-phenylalaninol dienamine. In a further embodiment, the reaction mixture is cooled to about 5° C. or less to facilitate crystallization.

In one embodiment, crystalline R-gossypol L-phenylalaninol dienamine is hydrolyzed to provide crude R-gossypol or R-gossypol acetic acid co-crystal. In a further embodiment, the hydrolysis of R-gossypol L-phenylalaninol dienamine is carried out at about 52° C. In a further embodiment, the hydrolysis of R-gossypol L-phenylalaninol dienamine is carried out in the absence of tetrahydrofuran. In a further embodiment, the hydrolysis of R-gossypol L-phenylalaninol dienamine is carried out in the presence of acetic acid, hydrochloric acid and water.

In one embodiment, R-gossypol or R-gossypol acetic acid co-crystals are isolated by filtration or centrifugation. In a further embodiment, R-gossypol or R-gossypol acetic acid co-crystals are washed with a solvent system comprising acetic acid and water. In a further embodiment, R-gossypol or R-gossypol acetic acid co-crystals are washed with water. In a further embodiment, R-gossypol or R-gossypol acetic acid co-crystals are dried in vacuo.

In one embodiment, R-gossypol acetic acid co-crystals are purified via crystallization in one or more solvent systems until the desired level of purity is achieved. In a further embodiment, R-gossypol acetic acid co-crystals are isolated by filtration or centrifugation. In a further embodiment, R-gossypol acetic acid co-crystals are washed with a solvent mixture. In a further embodiment, R-gossypol acetic acid co-crystals are dried in vacuo.

In one embodiment, crystallization of R-gossypol acetic acid co-crystals is carried out in a solvent system comprising ethyl acetate, ethanol, acetic acid and water. In a further embodiment, R-gossypol acetic acid co-crystals are washed with a solvent system comprising ethyl acetate, ethanol, acetic acid and water. In a further embodiment, R-gossypol acetic acid co-crystals are dried in vacuo.

In one embodiment, crystallization of R-gossypol acetic acid co-crystals is carried out in a solvent system comprising acetone, acetic acid and water.

In one embodiment, crystallization of R-gossypol acetic acid co-crystals is carried out in a solvent system comprising acetic acid and water. In a further embodiment, R-gossypol acetic acid co-crystals are washed with a solvent system comprising acetic and water. In a further embodiment, R-gossypol acetic acid co-crystals are dried in vacuo.

In one embodiment, R-gossypol acetic acid co-crystal is recrystallized one or more times in one or more solvent systems until the desired level of purity is achieved In one embodiment, a process for preparing R-(-)-gossypol acetic acid co-crystals is provided, the improvement comprising crystallizing a mixture of R- and S-gossypol L-phenylalaninol dienamine from a solvent system comprising acetonitrile and water and isolating crystalline R-gossypol L-phenylalaninol dienamine substantially free from said S-gossypol L-phenylalaninol dienamine; and preparing the R-(-)-gossypol acetic acid co-crystals.

In one embodiment, a process for preparing R-(-)-gossypol acetic acid co-crystals is provided, the improvement comprising: a) condensing gossypol with L-phenylalaninol in acetonitrile to provide a mixture of R- and S-gossypol L-phenylalaninol dienamine; b) adding water the reaction mixture at the completion of a) to obtain crystallized R-gossypol L-phenylalaninol dienamine; and c) isolating said crystalline R-gossypol L-phenylalaninol dienamine substantially free from said S-gossypol L-phenylalaninol dienamine; and preparing the R-(-)-gossypol acetic acid co-crystals.

The term "about," as used herein, includes the recited number ±10%. Thus, "about 10" means 9 to 11.

The term "purity," as used herein, refers to chemical and/or stereoisomeric (i.e., diastereomeric or enantiomeric) purity, unless otherwise indicated. The term "enantiomeric purity," as used herein, refers to a measure of the enantiomeric excess or ee of a chiral substance. The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})$ *100, where $[\alpha]_{obs}$ is the optical rotation of the mixture of enantiomers and $[\alpha]_{max}$ is the optical rotation of the pure enantiomer. The term "diastereomeric purity," as used herein, is defined by analogy to enantiomeric purity. Determination of diastereomeric or enantiomeric excess is possible using a variety of analytical techniques, including NMR spectroscopy, chiral column chromatography or optical polarimetry.

In one embodiment, R-(-)-gossypol acetic acid co-crystals have a purity of about 95%, 96%, 97%, 98%, 99% or 99.5% or more.

The term "substantially free," as used herein, refers to a composition comprising at least about 89% by weight of one stereoisomer (i.e., enantiomer or diastereomer) over the corresponding stereoisomer. In another embodiment, the composition comprises at least about 95%, 96%, 97%, 98%, 99% or 99.5% by weight of the preferred stereoisomer. Thus, the term "R-gossypol L-phenylalaninol dienamine substantially free from S-gossypol L-phenylalaninol dienamine," as used herein, refers to a composition of R-gossypol L-phenylalaninol dienamine comprising at least about 89% of R-gossypol L-phenylalaninol dienamine and at most about 11% of S-gossypol L-phenylalaninol dienamine by weight.

In one embodiment, R-(-)-gossypol acetic acid co-crystal comprises about 5%, 4%, 3%, 2%, 1% or 0.5% or less of (S)-(+)-gossypol.

The term "seeding," as used herein, refers to adding a small amount of a pure compound to a solution to help initiate crystallization of that compound from a solution. For example, adding crystalline R-gossypol L-phenylalaninol dienamine to a solution of R-gossypol L-phenylalaninol dienamine and S-gossypol L-phenylalaninol dienamine in solvent system comprising acetonitrile and water seeds the solution and initiates crystallization to provide crystalline R-gossypol L-phenylalaninol dienamine.

The term "R-gossypol L-phenylalaninol dienamine" or "R-gossypol L-phenylalaninol enamine-enamine," as used herein, refers to a composition comprising the compound derived from R-gossypol of structure:

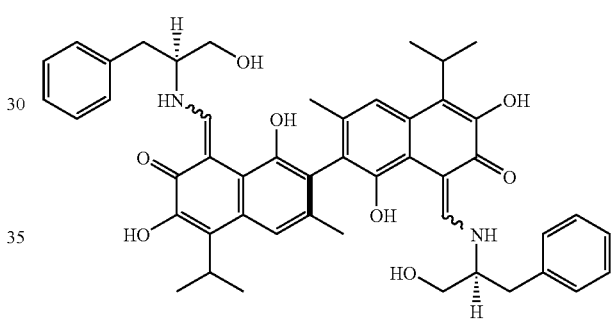

or a dienamine tautomer thereof.

The term "S-gossypol L-phenylalaninol dienamine" or "S-gossypol L-phenylalaninol enamine-enamine," as used herein, refers to a composition comprising the compound derived from S-gossypol of structure:

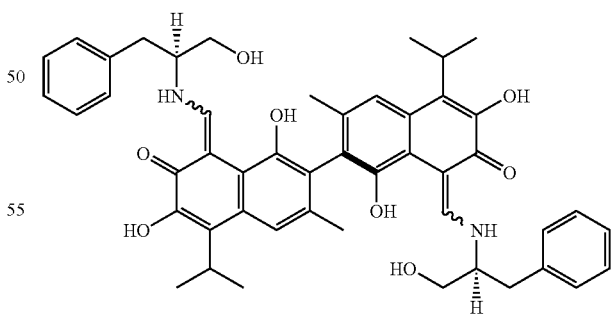

or a dienamine tautomer thereof.

The term "dienamine tautomer," as used herein, refers to all tautomeric forms of the condensation products between L-phenylalaninol and gossypol including, but not limited to, the bis oxazolidine tautomer 1, diimine (i.e., imine-imine) tautomer 2 and the imine-enamine tautomer 3.

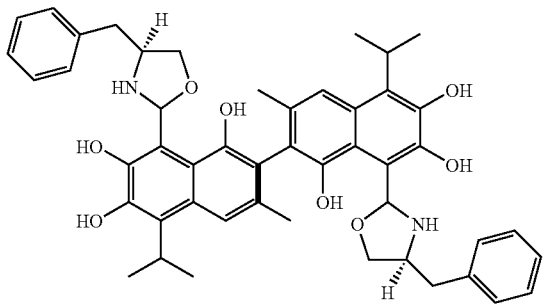

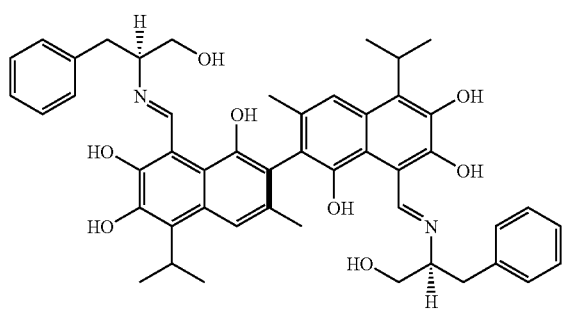

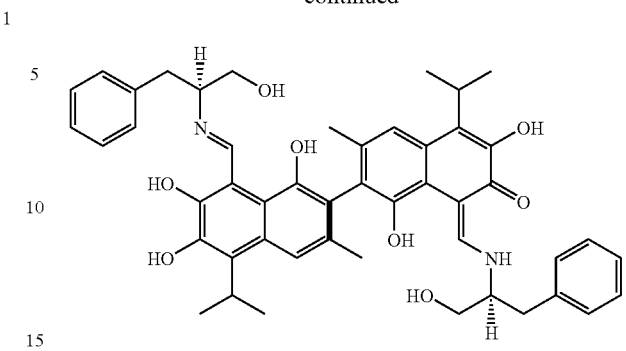

In one embodiment, the invention provides a composition consisting essentially of co-crystals of R-(−)-gossypol and acetic acid in a molar ratio of about 1:1 with a purity of about 95% or more. In another embodiment, the composition comprises about 96%, 97%, 98%, 99% or 99.5% or more of R-(−)-gossypol acetic acid co-crystal.

The following examples are illustrative, but not limiting, of the processes and methods of the present invention. Other suitable modifications and adaptations of the variety of reaction conditions and parameters normally encountered in synthetic organic and process chemistry and which are obvious to those skilled in the art are within the spirit and scope of the invention.

EXAMPLE 1

Preparation of a Mixture of R- and S-gossypol L-phenylalanine diimine

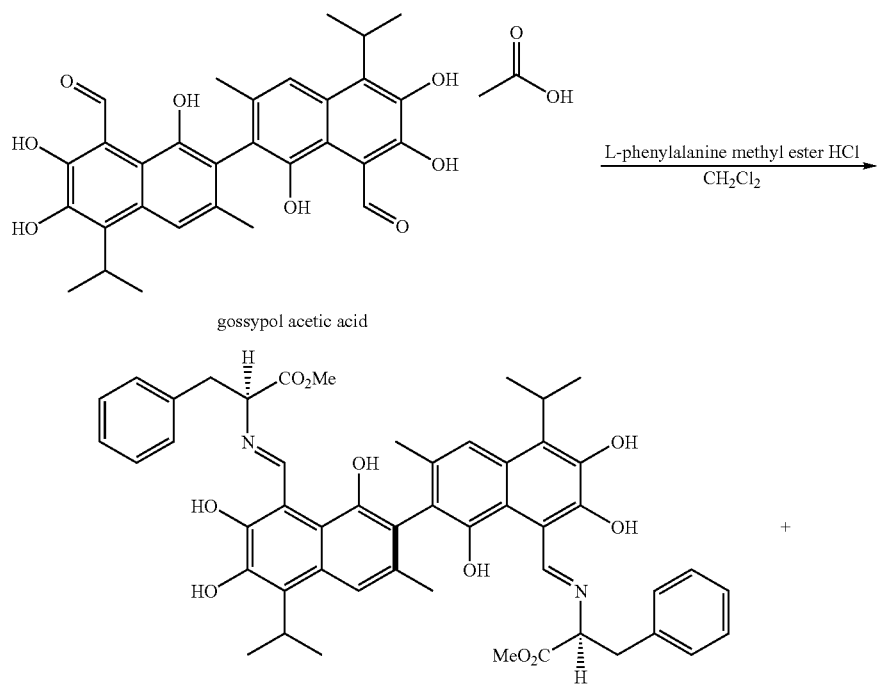

-continued

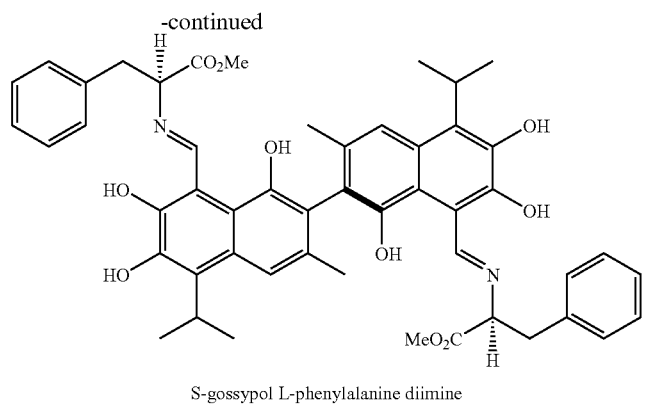

S-gossypol L-phenylalanine diimine

Step 1

L-Phenylalanine methyl ester hydrochloride (4.9 g) was dissolved in water (25 mL) in a 100 mL round bottom flask and stirred at room temperature. Sodium carbonate (3.1 g) in water (12.5 mL) was added in 3 minutes. The reaction mixture was stirred for 5 minutes at room temperature. Dichloromethane (25 mL) was added and the reaction mixture was stirred 5 minutes. The aqueous solution was transferred to a 125 mL separating funnel. The organic layer was collected. The aqueous layer was extracted twice with 12.5 mL of dichloromethane. The three organic extractions were combined, dried with magnesium sulfate (6 g), filtered to remove the magnesium sulfate and concentrated to give L-phenylalanine methyl ester free base.

Step 2

In a 250 mL flask equipped with a thermometer and under nitrogen, racemic gossypol acetic acid (5 g) was suspended in dichloromethane (50 mL). The free base of L-phenylalanine methyl ester from step 1 in dichloromethane was added to the racemic gossypol acetic acid suspension over the course of 5 minutes. The reaction mixture was stirred at room temperature for 15 minutes and magnesium sulfate (8.2 g) was added. Stirring was continued an additional 17 h. The reaction mixture was filtered to remove magnesium sulfate, concentrated and dried to give a diastereomeric mixture of R- and S-gossypol L-phenylalanine diimine.

EXAMPLE 2

Crystallization Study of R- and S-gossypol L-phenylalanine diimine

General protocol: In a 25 mL (one neck) round bottom flask, 0.2 to 0.6 g of a diastereomeric mixture of R- and S-gossypol L-phenylalanine diimine was introduced under nitrogen atmosphere. Then, 1 mL of solvent was added and the reaction mixture was heated at 50° C. The appropriate amount of solvent was introduced to obtain a limpid solution. After two hours at room temperature, a yellow precipitate that formed was filtered and the crystalline product was analyzed by HPLC. Results are presented in Table 1. For brevity, "R" denotes R-gossypol L-phenylalanine diimine and "S" denotes S-gossypol L-phenylalanine diimine. DCM=dichloromethane; iPrOH=isopropanol; MeOH=methanol; THF=tetrahydrofuran; TBME=tert-butyl methyl ether; MeCN=acetonitrile.

TABLE 1

| Entry | Solvent system | Initial weight R- and S- gossypol phenylalanine diimine mixture (g) | Initial R:S ratio (HPLC) | Crystalline yield (g) | R:S ratio in crystalline Product (HPLC) |
|---|---|---|---|---|---|
| 1 | 1:2 DCM:iPrOH | 0.62 | 49.1/50.1 | 0.341 | 62.6/36.5 |
| 2 | 1:1 DCM:iPrOH | 0.50 | 49.1/50.1 | 0.119 | 65.0/34.4 |
| 3 | 2:1 DCM:iPrOH | 0.26 | 49.1/50.1 | No crystal formation | |
| 4 | 1:2 DCM:MeOH | 0.50 | 49.1/50.1 | 0.308 | 61.4/37.8 |
| 5 | 1:2 DCM:EtOH | 0.50 | 49.1/50.1 | 0.311 | 50.7/48.3 |
| 6 | 1:5:1.5 DCM:hexane:heptane | 0.25 | 48.7/50.4 | 0.171 | 60.5/38.5 |
| 7 | 2:1 MeOH:water | 0.50 | 49.1/50.1 | 0.225 | 48.6/50.0 |
| 8 | 2:1 MeOH:hexane | 0.27 | 48.7/50.4 | 0.100 | 63.4/35.7 |
| 9 | 2:1 EtOH:hexane | 0.25 | 48.7/50.4 | 0.134 | 64.4/34.5 |

TABLE 1-continued

| Entry | Solvent system | Initial weight R- and S-gossypol phenylalanine diimine mixture (g) | Initial R:S ratio (HPLC) | Crystalline yield (g) | R:S ratio in crystalline Product (HPLC) |
|---|---|---|---|---|---|
| 10 | 2:1 Water:THF | 0.20 | 48.7/50.4 | No crystal formation | |
| 11 | Toluene | 0.50 | 49.1/50.1 | 0.245 | 62.9/36.1 |
| 12 | 1:1 Toluene:heptane | 0.21 | 48.7/50.4 | 0.112 | 60.9/34.1 |
| 13 | MeCN | 0.50 | 49.1/50.1 | 0.238 | 64.2/35.1 |
| 14 | 10:1 MeCN:water | 0.21 | 48.7/50.4 | 0.1071 | 61.6/37.2 |
| 15 | TBME | 0.50 | 49.1/50.1 | 0.278 | 63.3/36.1 |
| 16 | TBME:heptane | 0.20 | 48.7/50.4 | 0.067 | 63.8/34.9 |

Thus, at best, a R:S ratio of about 65:35 was obtained with 1:1 DCM:iPrOH. Three successive crystallizations of a mixture of R- and S-gossypol L-phenylalanine diimine in 1:2 DCM:iPrOH did not lead to significant improvement in the R:S ratio (Table 2).

TABLE 2

| Entry | Solvent system | Initial weight R- and S-gossypol phenylalanine diimine mixture (g) | Initial R:S ratio (HPLC) | Crystalline yield (g) | R:S ratio in crystalline Product (HPLC) |
|---|---|---|---|---|---|
| 1 | 1:2 DCM:iPrOH | 0.62 | 49.1/50.1 | 0.341 | 62.6/36.5 |
| 2 | 1:2 DCM:iPrOH | 0.34 | 62.6/36.5 | 0.212 | 65.6:33.7 |
| 3 | 1:2 DCM:iPrOH | 0.21 | 65.6:33.7 | 0.142 | 65.9:33.7 |

EXAMPLE 3

Preparation of R- and S-gossypol-L-phenylaninol dienamine

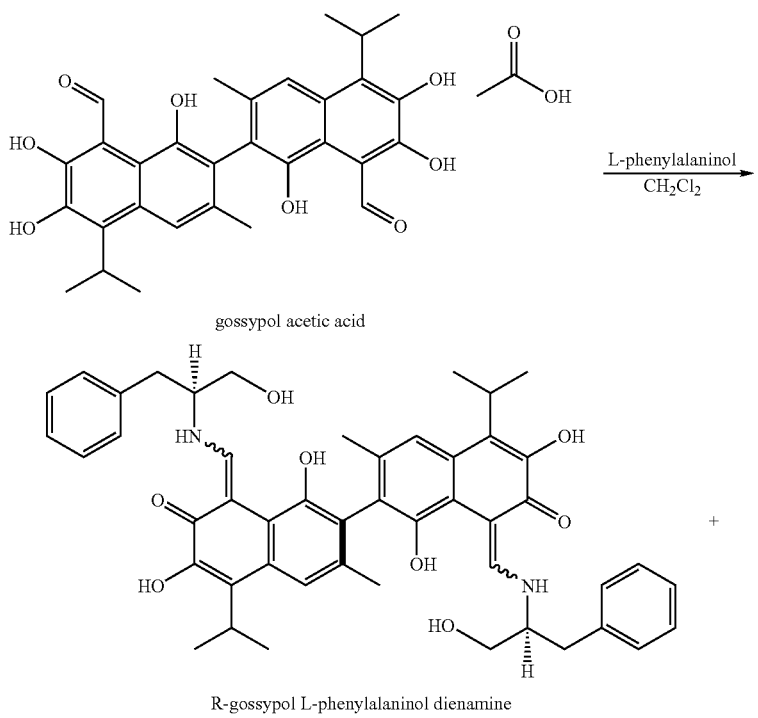

Scheme 2 gossypol acetic acid

R-gossypol L-phenylaninol dienamine

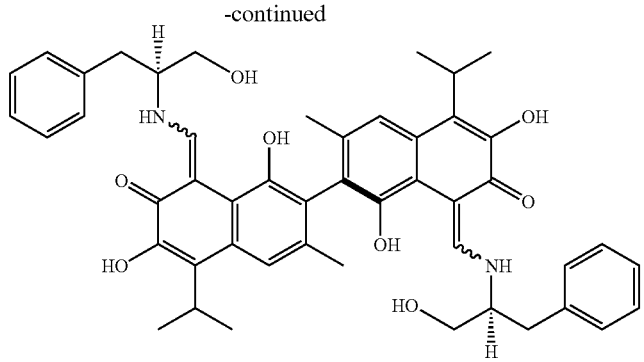

S-gossypol L-phenylalaninol dienamine

Racemic gossypol acetic acid (0.276 g) was treated with dichloromethane (1.05 mL) followed by L-phenylalaninol (0.1515 g) and allowed to stir at 25° C. for 17 h. The reaction mixture was dried with magnesium sulfate, filtered and concentrated to dryness to give 0.352 g of R- and S-gossypol-L-phenylalaninol dienamine as a brown solid.

EXAMPLE 4

Crystallization Study of R- and S-gossypol phenylalaninol dienamine

General protocol: In a 25 mL (one neck) round bottom flask, 0.2 to 1.1 g of a diastereomeric mixture of R- and S-gossypol L-phenylalaninol dienamine was introduced under nitrogen atmosphere. Then, 1 mL of solvent was added and the reaction mixture was heated at 50° C. The appropriate amount of solvent was introduced to obtain a limpid solution. After two hours at room temperature, the yellow precipitate that formed was filtered and the crystalline product was analyzed by HPLC. Results are presented in Table 3. For brevity, "R" denotes R-gossypol L-phenylalaninol dienamine and "S" denotes S-gossypol L-phenylalaninol dienamine. DCM=dichloromethane; iPrOH=isopropanol; MeOH=methanol; THF=tetrahydrofuran; TBME=tert-butyl methyl ether; MeCN=acetonitrile.

TABLE 3

| Entry | Solvent(s) | Initial weight R- and S- gossypol phenylalaninol dienamine mixture (g) | Initial R:S Ratio (HPLC) | Crystalline yield (g) | R:S ratio in crystalline product (HPLC) |
|---|---|---|---|---|---|
| 1 | MeOH | 1.05 | 49.4/49.7 | 0.702[a] | 50.1/49.9 |
| 2 | iPrOH | 0.65 | 49.4/49.7 | 0.422 | 49.2/50.8 |
| 3 | Acetone | 0.64 | 49.4/49.7 | No crystal formation | |
| 4 | Toluene | 1.10 | 49.4/49.7 | 0.628 | 49.4/50.6 |
| 5 | 1:1 Toluene:heptane | 0.21 | 49.7/50.0 | No crystal formation | |
| 6 | 2:1 TBME:heptane | 0.21 | 49.7/50.0 | No crystal formation | |
| 7 | 2:1 MeOH:hexane | 0.32 | 49.7/50.0 | No crystal formation | |
| 8 | 1:1 DCM:hexane | 0.25 | 49.7/50.0 | No crystal formation | |
| 9 | 5:1 THF:water | 0.20 | 49.7/50.0 | No crystal formation | |
| 10 | 1:1 MeOH:water | 0.20 | 49.7/50.0 | No crystal formation | |
| 11 | CH$_3$CN | 1.01 | 49.4/49.7 | 0.530 | 50.1/49.9 |
| 12 | 5:1 CH$_3$CN:water | 0.20 | 49.7/50.0 | 0.058 | 88.7/11.3 |
| 13 | 5:1 CH$_3$CN:water[b]: | 0.50 | 49.7/50.0 | 0.122 | 98.3/1.7 |

[a]For this experiment, seeding with R-gossypol L-phenylalaninol dienamine was attempted.
[b]The precipitate was washed two times with 5:1 acetonitrile:water. This trial was performed twice and the same results were obtained.

Thus, a solvent system comprising acetonitrile and water provided R-gossypol L-phenylalaninol dienamine substantially free from S-gossypol L-phenylalaninol dienamine with an R:S ratio of about 89:11. Other solvent systems resulted in no enrichment of diastereomeric purity or no crystal formation.

EXAMPLE 5

Crystallization Studies in acetonitrile:Water Mixtures

General protocol: Referring to Table 4, a mixture of R- and S-gossypol L-phenylalaninol dienamine (gossypol dienamine; amount) was soublized in acetonitrile at 21° C.-25° C. and water was added drop wise over the period of time indicated in a) to achieve the desired acetonitrile:water ratio. R-gossypol L-phenylalaninol dienamine crystallized and was filtered through a sintered funnel after the period of time and temperature indicated in b). The isolated crystalline R-gossypol L-phenylalaninol dienamine was washed with the same ratio of solvent used for crystallization as indicated in c) and dried in vacuo.

TABLE 4

| Amount gossypol dienamine (g) | $CH_3CN:H_2O$ ratio | Protocol | Yield of R-isomer | HPLC purity |
|---|---|---|---|---|
| 0.5 | 5:1 | a) addition of water for 4 min at 25° C. b) 3.3 h of stirring at 26° C. c) washing with 2 × 3 mL | 30% | 97.4% |
| 0.5 | 5:1.5 | a) addition of water for 30 min at 26° C. b) 20 min of stirring at 26° C. c) washing with 2 × 3 mL | 41% | 98.8% |
| 0.5 | 5:2 | a) addition of water for 21 min at 25° C. b) 25 min of stirring at 25° C. c) washing with 2 × 3 mL | 61% | 98.1% |

TABLE 4-continued

| Amount gossypol dienamine (g) | $CH_3CN:H_2O$ ratio | Protocol | Yield of R-isomer | HPLC purity |
|---|---|---|---|---|
| 0.5 | 5:2 | a) addition of water for 16 min at 25° C. b) 25 min of stirring at 5° C. c) washing with 4 × 1.5 mL | 81% | 93.9% |
| 0.5 | 5:1.5 | a) addition of water for 13 min at 25° C. b) 1 h of stirring at 5° C. c) washing with 1 × 1.5 mL | 68% | 93.6% |
| 0.5 | 5:1 | a) addition of water for 11 min at 25° C. b) 0.5 h of stirring at 5° C. c) washing with 3 × 1.5 mL | 66.4% | 98.0% |
| 4.55 | 5:1 | a) addition of water for 20 min at 21° C. b) 40 min of stirring at 5° C. c) washing with 2 × 5 mL | 71% | 98.4% |

The crystallization of R- and S-gossypol L-phenylalaninol dienamine in acetonitrile:water from 5:1 to 5:2 at 25-26° C. gave R-gossypol L-phenylalaninol dienamine with purities between 97.4% and 98.8%. Under these conditions, yields improved to 61% with a higher proportion of water. At 5° C., R-gossypol L-phenylalaninol dienamine was obtained with good purity and higher yields. The process was effectively scaled-up to 4.55 g of R- and S-gossypol L-phenylalaninol dienamine to give R-gossypol L-phenylalaninol dienamine in 71% yield and 98.4% purity. These experiments confirmed that R-gossypol L-phenylalaninol dienamine can be isolated substantially free from S-gossypol L-phenylalaninol dienamine using a solvent mixture comprising acetonitrile and water.

EXAMPLE 6

Development of One Pot Synthesis/Crystallization Protocol in acetonitrile

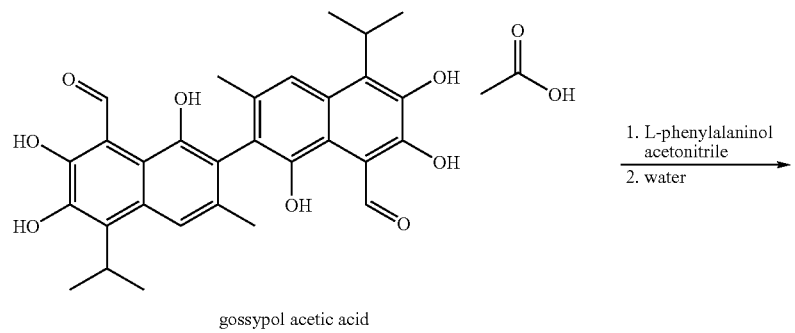

gossypol acetic acid

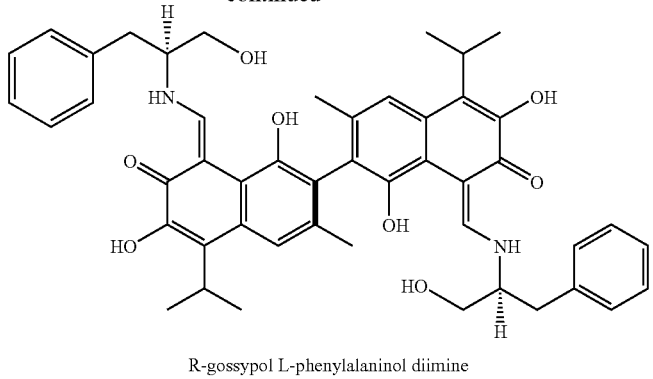

R-gossypol L-phenylalaninol diimine

Protocol as illustrated by experimental details of Entry 3 in Table 5: Racemic gossypol acetic acid (79.7 g, 137.7 mmol) and L-phenylalaninol (43.7 g, 289.3 mmol, 2.1 eq.) were introduced in a 2 L glass reactor filled with nitrogen. Acetonitrile (1.08 L) was poured on the powder and the mixture was heated at 30° C. for 2.6 h. The solution was cooled to 25° C. and water (217 mL) was added drop wise. Yellow brown crystals appeared during the addition of water. The suspension was cooled to 5° C. and stirred for 1 h. The suspension was filtered through a sintered funnel and washed twice with 1:1 acetonitrile:water at 5° C. (160 mL). The solid was dried in vacuo at 25° C. for 24 h to give 45.0 g of R-gossypol L-phenylalaninol dienamine as a yellow brown powder. HPLC purity is 99.2%.

TABLE 5

| Entry | Amount gossypol acetic acid | Protocol | Yield of R-isomer | HPLC purity |
|---|---|---|---|---|
| 1 | 0.5 g | a) 30° C. for 3.1 h<br>b) addition of water for 7 min at 25° C.; (5:1 CH$_3$CN:H$_2$O)<br>c) 50 min of stirring at 5° C.<br>d) washing with 1 × 2 mL | 81% | 97.3% |
| 2 | 10.0 g | a) 30° C. for 3.1 h<br>b) addition of water for 22 min at 23° C.; (5:1 CH$_3$CN:H$_2$O)<br>c) 1.1 h of stirring at 5° C.<br>d) washing with 2 × 20 mL | 81% | 97.2% |
| 3 | 79.7 g | a) 30° C. for 2.7 h<br>b) addition of water for 30 min at 23° C.; (5:1 CH$_3$CN:H$_2$O)<br>c) 1 h of stirring at 5° C.<br>d) washing with 2 × 160 mL | 83% | 99.2% |

Thus, a one pot synthesis/crystallization protocol provided an effective means of isolating R-gossypol L-phenylalaninol dienamine substantially free from S-gossypol L-phenylalaninol dienamine. Starting from about 80 g of gossypol acetic acid, R-gossypol L-phenylalaninol dienamine was obtained in 83% yield and 99.2% purity.

EXAMPLE 7

Reproducibility of R-gossypol phenylalaninol dienamine Crystallization

General protocol: Referring to Table 6, racemic gossypol acetic acid (amount) and L-phenylalaninol (2.1 equiv.) were combined in acetonitrile at 30° C. and stirred for the indicated period of time. In each experiment the acetonitrile:water ratio was about 5:1 and seeding was with crystalline R-gossypol L-phenylalaninol dienamine at the temperature indicated. The isolated crystalline R-gossypol L-phenylalaninol dienamine was washed with about 5:1 acetonitrile:water. Purities are determined by HPLC.

TABLE 6

| Amount gossypol acetic acid | Protocol | Yield of R-isomer | HPLC purity of R-isomer | HPLC chemical purity |
|---|---|---|---|---|
| 20.0 g | a) 30° C. for 2.5 h<br>b) addition of water for 7 min at 50° C.<br>c) seeding at 37° C.<br>d) slow cooling to 33° C. and rapid cooling to 5° C.<br>e) 5 min of stirring at 5° C.<br>f) washing with 2 × 27 mL at 5° C.<br>g) drying 16 h at 30° C.<br>h) storage under air and light | Quant. (residual CH$_3$CN = 13.9%) | 97.3%<br>96.0%[a] | 98.0%<br>98.4%[a] |
| 20.5 g | a) 30° C. for 3.25 h<br>b) addition of water for 7 min at 50° C.<br>c) seeding at 39° C.<br>d) slow cooling to 33° C. and rapid cooling to 5° C.<br>e) 1 h of stirring at 5° C.<br>f) washing with 2 × 28 mL at 5° C.<br>g) drying 16 h at 30° C.<br>h) storage under air and light | 92% (residual CH$_3$CN = 1.45%) | 97.8% | 98.6% |

TABLE 6-continued

| Amount gossypol acetic acid | Protocol | Yield of R-isomer | HPLC purity of R-isomer | HPLC chemical purity |
|---|---|---|---|---|
| 21.7 g | a) 30° C. for 3.75 h<br>b) addition of water for 7 min at 50° C.<br>c) seeding at 35° C.<br>d) slow cooling to 33° C. and rapid cooling to 5° C.<br>e) 0.5 h of stirring at 5° C.<br>f) washing with 2 × 29 mL at 5° C.<br>g) drying 16 h at 30° C. | Quant. (residual CH$_3$CN = 21.5% | 98.0% | 98.3% |

[a] After storage at room temperature without protection against air and light for several days.

Thus, crystallization of R-gossypol L-phenylalaninol dienamine from a solvent system comprising about 5:1 acetonitrile:water was reproducible when seeded with pure R-gossypol L-phenylalaninol dienamine. In each case, good diastereomeric and chemical purity was obtained.

EXAMPLE 8

Large-scale Preparation of R-gossypol-L-phenylaninol dienamine

Racemic gossypol acetic acid (152.8 g, 1.0 eq) and L-phenylalaninol (83.9 g, 2.1 eq.) were dissolved in acetonitrile (1039 mL) and heated at 30° C. for 2.5 h under nitrogen. The mixture was then heated to 50° C. and water (208 mL, 1.4 eq. w/w) was added. The solution was cooled to 37° C. and seeded with pure R-gossypol-L-phenylalaninol (0.518 g, 0.5% w/w). The mixture was cooled to 5° C. The suspension was filtered, washed with acetonitrile:water (5:1, 208 mL) at 5° C. and dried in vacuo at 30° C. to give crystalline R-gossypol L-phenylalaninol dienamine as a brownish orange solid (90.5 g, 87%). HPLC analysis indicated a diastereomeric R:S ratio of 98.5:1.5.

If further purification is desired, R-gossypol L-phenylalaninol dienamine (59.0 g) obtained according to the method of Example 8 (above) is solublized in 5:1 acetonitrile:water (563 mL) at 60° C. The solution is cooled to 47° C., seeded with pure R-gossypol-L-phenylalaninol (0.087 g) and cooled to 5° C. The resulting suspension is filtered, washed twice with 5:1 acetonitrile:water (94 mL) at 5° C. and dried in vacuo at 30° C. to give crystalline R-gossypol-L-phenylaninol dienamine as a brownish orange solid (34.1 g, 73%). HPLC analysis indicated a purity of 99.2%.

If further purification is desired, additional crystallizations can be performed.

EXAMPLE 9

Preparation of R-gossypol acetic acid

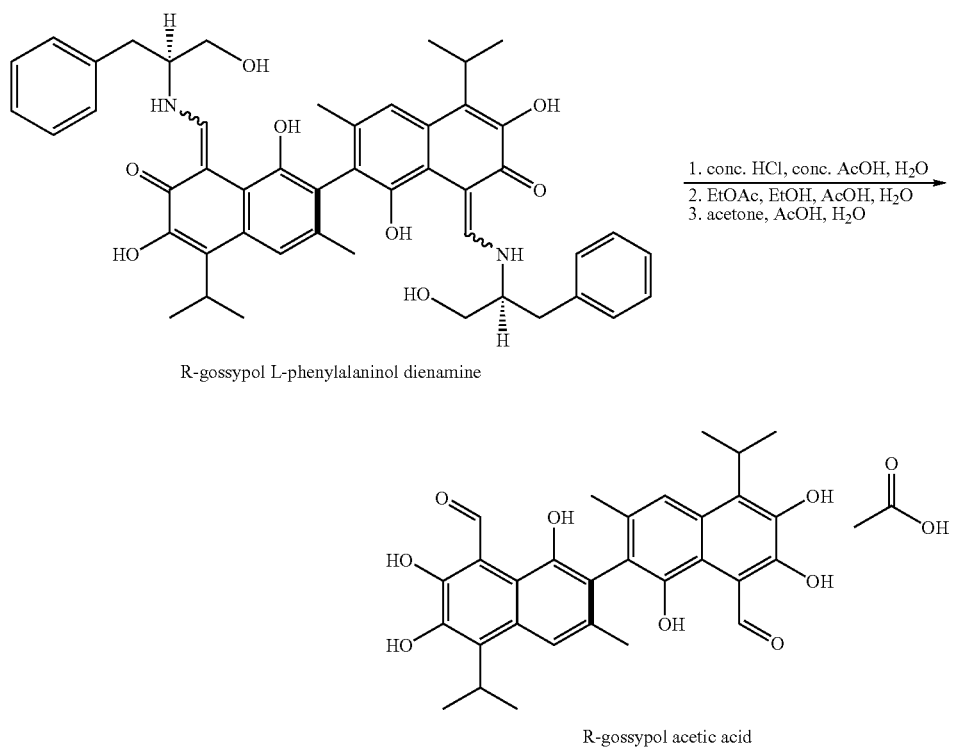

Step 1—Hydrolysis

R-gossypol L-phenylalaninol dienamine (100 g, 1.0 eq.) was dissolved in glacial acetic acid (850 mL) at 52° C. Water (212.5 mL, 2.1 eq. w/w) was added followed by concentrated HCl (41.0 mL, 8 eq.). Once the mixture was stirred at 52° C. for 3.5 h, water (425 mL, 4.2 eq. w/w) was added slowly to the mixture. The suspension was cooled to 20° C., filtered, washed with acetic acid:water (1:1, 100 mL) and with water (100 mL), and dried in vacuo at 20° C. to give R-gossypol acetic acid co-crystals as a yellow solid (104.7 g). HPLC purity is 97.23%.

Step 2—Purification

R-gossypol acetic acid co-crystals (73.71 g, 1.0 eq) were dissolved in ethyl acetate (287 mL) and ethanol (59 mL) at 20° C. The solution was filtered and rinsed with ethyl acetate (96 mL), acetic acid (260 mL) and water (64 mL). The solution was concentrated in vacuo below 30° C. to remove at least 80% of the total volume of ethyl acetate and ethanol. Acetic acid:water (1:1, 147 mL) was added and the suspension was stirred at 20° C. for 30 minutes, filtered and washed three times with acetic acid:water (1:1, 74 mL). R-gossypol acetic acid co-crystals were obtained as a yellow solid (179.4 g) and used directly in the next step.

If further purification is desired, R-gossypol acetic acid co-crystals (73.71 g) obtained from the method of Example 9, step 2 (above), ethyl acetate (383 mL), ethanol (59 mL) and acetic acid (260 mL) are stirred at 20° C. Water (64 mL) is added and the suspension is concentrated in vacuo below 30° C. to remove at least 80% of the total volume of ethyl acetate and ethanol. Acetic acid:water (1:1, 147 mL) is added and the suspension is stirred at 20° C. for 30 minutes, filtered and washed with acetic acid:water (1:1, 74 mL) at 20° C. R-gossypol acetic acid co-crystals are obtained as a yellow solid (119.1 g).

If further purification is desired, additional crystallizations can be performed.

Step 3—Solvent Exchange

R-(−)-gossypol acetic acid co-crystals (73.71 g, 1.0 eq.) were suspended in acetone (590 mL), treated with acetic acid (295 mL) and stirred at 20° C. Water (295 mL) was added and the solution was concentrated in vacuo at <30° C. to remove >80% of the volume of acetone. The suspension was stirred at 20° C., filtered and washed with acetic acid:water (1:1, 100 mL). R-gossypol acetic acid co-crystals were obtained as a yellow solid (80.0 g) and used directly in the next step.

EXAMPLE 10

Preparation of R-gossypol acetic acid co-crystal

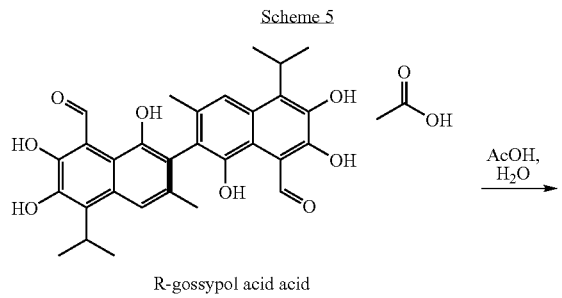

R-gossypol acid acid

Scheme 5

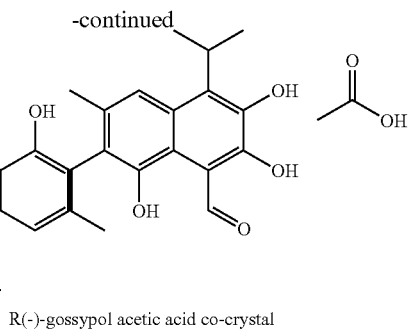

R(-)-gossypol acetic acid co-crystal

R-gossypol acetic acid co-crystals (73.71 g, 1.0 eq.) were partially dissolved in acetic acid (295 mL) and stirred at 20° C. for 3 h at which time water (295 mL) was added. The resulting suspension was filtered and washed with acetic acid:water (1:1, 100 mL). The isolated material was dried in vacuo at 20° C. to give R-gossypol acetic acid co-crystals as a yellow solid (54.2 g, 73% yield, 98.82% purity).

If further purification is desired, additional crystallizations can be performed.

The aforementioned Examples demonstrate the difficulty encountered in developing a process for obtaining R-(−)-gossypol and its acetic acid co-crystal. Two different diastereomeric gossypol derivatives were prepared in an effort to separate by crystallization the two diastereomers. As illustrated in Example 2, attempts to resolve a mixture of R- and S-gossypol L-phenylalanine diimine by crystallization were not successful. In this study, a variety of solvent systems were tested. Modest diastereomeric enrichment was observed in some cases.

As illustrated in Example 4, it was unexpectedly discovered that R-gossypol L-phenylalaninol dienamine could be isolated in high diastereomeric purity from a mixture of R- and S-gossypol L-phenylalaninol dienamine via crystallization in a solvent system comprising acetonitrile and water. All other solvent systems yielded unsatisfactory results. Most solvent systems resulted in no crystal formation. Based on this discovery, a reproducible one-pot process to isolate crystalline R-gossypol L-phenylalaninol dienamine was developed (Examples 5 to 7). This facilitated the large-scale preparation of R-(−)-gossypol acetic acid co-crystals as demonstrated in Examples 8 to 10.

Having now fully described the invention, it will be understood by those of skill in the art that the same can be performed within a wide and equivalent range of conditions and other reaction parameters without affecting the scope of the invention or any embodiment thereof. All patents, patent applications and publications cited herein are fully incorporated by reference herein in their entirety.

What is claimed is:

1. A process for preparing R-gossypol L-phenylalaninol dienamine from a mixture of R- and S-gossypol L-phenylalaninol dienamine comprising crystallizing said mixture from a solvent system comprising acetonitrile and water and isolating crystalline R-gossypol L-phenylalaninol dienamine substantially free from said S-gossypol L-phenylalaninol dienamine.

2. The process of claim 1 wherein said crystalline R-gossypol L-phenylalaninol dienamine is isolated by filtration.

3. The process of claim 1 wherein the acetonitrile:water ratio is about 5:1.

4. The process of claim 3 wherein the acetonitrile:water ratio is 5:1.

5. The process of claim 1 further comprising:
a) washing said crystalline R-gossypol L-phenylalaninol dienamine with a solvent system comprising acetonitrile and water; and
b) drying said crystalline R-gossypol L-phenylalaninol dienamine in vacuo.

6. A process for preparing R-gossypol L-phenylalaninol dienamine comprising:
a) condensing gossypol with L-phenylalaninol in acetonitrile to provide a mixture of R- and S-gossypol L-phenylalaninol dienamine;
b) adding water to the reaction mixture at the completion of a) to obtain crystallized R-gossypol L-phenylalaninol dienamine; and
c) isolating said crystalline R-gossypol L-phenylalaninol dienamine substantially free from said S-gossypol L-phenylalaninol dienamine.

7. The process of claim 6 wherein said crystalline R-gossypol L-phenylalaninol dienamine is isolated by filtration.

8. The process of claim 6 wherein the acetonitrile:water ratio in b) is about 5:1.

9. The process of claim 8 wherein the acetonitrile:water ratio is 5:1.

10. The process of claim 6 further comprising:
a) washing said crystalline R-gossypol L-phenylalaninol dienamine with a solvent system comprising acetonitrile and water; and
b) drying said crystalline R-gossypol L-phenylalaninol dienamine in vacuo.

11. The process of claim 1 or 6 wherein said crystallization is induced by seeding with crystalline R-gossypol L-phenylalaninol dienamine.

12. The process of claim 1 or 6 wherein said crystalline R-gossypol L-phenylalaninol dienamine has a purity of about 90% or more.

13. The process of claim 12 wherein said purity is about 95% or more.

14. The process of claim 13 wherein said purity is about 98% or more.

15. The process of claim 12 wherein said purity is about 99% or more.

16. In a process for preparing R-(−)-gossypol acetic acid co-crystals, the improvement comprising crystallizing a mixture of R- and S-gossypol L-phenylalaninol dienamine from a solvent system comprising acetonitrile and water and isolating crystalline R-gossypol L-phenylalaninol dienamine substantially free from said S-gossypol L-phenylalaninol dienamine; and preparing the R-(−)-gossypol acetic acid co-crystals.

17. The process of claim 16, further comprising isolating said crystalline R-gossypol L-phenylalaninol dienamine by filtration.

18. The process of claim 16, wherein the acetonitrile:water ratio is about 5:1.

19. The process of claim 18, wherein the acetonitrile:water ratio is 5:1.

20. The process of claim 16, further comprising:
a) washing said crystalline R-gossypol L-phenylalaninol dienamine with a solvent system comprising acetonitrile and water; and
b) drying said crystalline R-gossypol L-phenylalaninol dienamine in vacuo.

21. In a process for preparing R-(−)-gossypol acetic acid co-crystals, the improvement comprising:
a) condensing gossypol with L-phenylalaninol in acetonitrile to provide a mixture of R- and S-gossypol L-phenylalaninol dienamine;
b) adding water to the reaction mixture at the completion of a) to obtain crystallized R-gossypol L-phenylalaninol dienamine; and
c) isolating said crystalline R-gossypol L-phenylalaninol dienamine substantially free from said S-gossypol L-phenylalaninol dienamine; and
preparing the R-(−)-gossypol acetic acid co-crystals.

22. The process of claim 21, further comprising isolating said crystalline R-gossypol L-phenylalaninol dienamine by filtration.

23. The process of claim 21, wherein the acetonitrile:water ratio is about 5:1.

24. The process of claim 23, wherein the acetonitrile:water ratio is 5:1.

25. The process of claim 21, further comprising:
a) washing said crystalline R-gossypol L-phenylalaninol dienamine with a solvent system comprising acetonitrile and water; and
b) drying said crystalline R-gossypol L-phenylalaninol dienamine in vacuo.

* * * * *